(12) United States Patent
Koenig et al.

(10) Patent No.: US 7,833,208 B2
(45) Date of Patent: Nov. 16, 2010

(54) MULTILAYER ABSORBENT ARTICLE

(75) Inventors: David W. Koenig, Menasha, WI (US);
Wael R. Joseph, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 119 days.

(21) Appl. No.: 11/025,723

(22) Filed: Dec. 29, 2004

(65) Prior Publication Data
US 2006/0142722 A1 Jun. 29, 2006

(51) Int. Cl.
*A61F 13/47* (2006.01)
*A61F 13/02* (2006.01)

(52) U.S. Cl. ............... 604/385.03; 604/307; 604/344

(58) Field of Classification Search ............. 604/307, 604/385.03, 387
See application file for complete search history.

(56) References Cited

U.S. PATENT DOCUMENTS

| | | | |
|---|---|---|---|
| 2,123,750 A * | 7/1938 | Schulz | 604/365 |
| 2,273,995 A * | 2/1942 | Rogerson et al. | 264/112 |
| 2,306,406 A * | 12/1942 | Robinson | 604/364 |
| 2,817,335 A * | 12/1957 | Thompson | 604/307 |
| 3,081,771 A * | 3/1963 | Lee | 604/344 |
| 3,135,262 A * | 6/1964 | Kobler et al. | 604/385.18 |
| 3,464,413 A * | 9/1969 | Alvin et al. | 604/306 |
| 3,490,454 A * | 1/1970 | Alvin et al. | 604/359 |
| 3,521,637 A * | 7/1970 | Waterbury | 604/286 |
| 3,585,998 A * | 6/1971 | Hayford et al. | 604/359 |
| 3,598,122 A * | 8/1971 | Zaffaroni | 424/435 |
| 3,749,094 A * | 7/1973 | Duncan | 604/15 |
| 3,813,695 A * | 6/1974 | Podell et al. | 2/168 |
| 3,911,501 A * | 10/1975 | Seltzer | 2/167 |
| 3,976,075 A * | 8/1976 | Chinai et al. | 604/365 |
| 4,031,894 A * | 6/1977 | Urquhart et al. | 424/448 |
| 4,336,804 A * | 6/1982 | Roeder | 604/387 |

(Continued)

FOREIGN PATENT DOCUMENTS

EP 0 485 744 B1 1/1996

(Continued)

OTHER PUBLICATIONS

Marks' Standard Handbook for Mechanical Engineers, pp. 3-21 to 3-24, Avallone, E.A. et al., 10th Ed., 1996.*

(Continued)

*Primary Examiner*—Tatyana Zalukaeva
*Assistant Examiner*—Paula L Craig
(74) *Attorney, Agent, or Firm*—Armstrong Teasdale, LLP

(57) ABSTRACT

An article for use in contact with a tissue layer of a person and capable of holding its position with respect to the contacted tissue layer while reducing the opportunity for damage to the tissue layer comprises a support structure and a contact layer associated with the support structure. The contact layer has an engagement surface adapted to contact the user's tissue layer. The contact layer is constructed so that the engagement surface has a first state adapted to inhibit movement of the article with respect to the tissue layer of the user, and a second state adapted to enhance movement of the article with respect to the tissue layer of the user. The engagement surface is adapted to transform from the first state to the second state upon application of a force greater than a threshold force.

16 Claims, 10 Drawing Sheets

U.S. PATENT DOCUMENTS

| | | | | |
|---|---|---|---|---|
| 4,341,211 | A * | 7/1982 | Kline | 604/514 |
| 4,347,843 | A * | 9/1982 | De Zaepffel | 604/345 |
| 4,762,738 | A * | 8/1988 | Keyes et al. | 428/34.3 |
| 4,908,027 | A * | 3/1990 | Enscore et al. | 604/890.1 |
| 4,913,896 | A * | 4/1990 | Harvey | 424/69 |
| 4,959,059 | A * | 9/1990 | Eilender et al. | 604/358 |
| 5,012,801 | A | 5/1991 | Feret | |
| 5,167,649 | A * | 12/1992 | Zook | 604/307 |
| 5,232,769 | A * | 8/1993 | Yamato et al. | 442/123 |
| 5,250,344 | A * | 10/1993 | Williamson et al. | 428/143 |
| 5,364,339 | A * | 11/1994 | Carver | 602/47 |
| 5,395,666 | A * | 3/1995 | Brindle | 428/36.4 |
| 5,476,440 | A * | 12/1995 | Edenbaum | 602/8 |
| 5,658,270 | A * | 8/1997 | Lichstein | 604/387 |
| 5,752,278 | A | 5/1998 | Gunn | |
| 5,795,636 | A * | 8/1998 | Keller et al. | 428/40.1 |
| 5,899,207 | A | 5/1999 | Scheinberg | |
| 5,951,534 | A * | 9/1999 | Cummings et al. | 604/359 |
| 6,007,837 | A * | 12/1999 | Enscore et al. | 424/449 |
| 6,083,616 | A * | 7/2000 | Dressler | 428/323 |
| 6,117,803 | A * | 9/2000 | Morman et al. | 442/381 |
| 6,177,171 | B1 | 1/2001 | Constantinides | |
| 6,358,235 | B1 * | 3/2002 | Osborn et al. | 604/385.18 |
| 6,362,387 | B1 | 3/2002 | Carlson et al. | |
| 6,395,955 | B1 * | 5/2002 | Roe et al. | 604/361 |
| 6,503,620 | B1 * | 1/2003 | Xie et al. | 428/354 |
| 6,559,353 | B1 * | 5/2003 | Sheridan | 604/367 |
| 6,746,418 | B1 * | 6/2004 | Pauley et al. | 604/12 |
| 6,746,433 | B1 * | 6/2004 | Shimoe et al. | 604/385.01 |
| 6,904,615 | B2 * | 6/2005 | Kobe et al. | 2/161 |
| 7,087,806 | B2 * | 8/2006 | Scheinberg et al. | 602/41 |
| 7,345,215 | B2 * | 3/2008 | Fernfors et al. | 604/378 |
| 7,396,976 | B2 * | 7/2008 | Hurwitz et al. | 602/58 |
| 2002/0086142 | A1 * | 7/2002 | Ewings et al. | 428/202 |
| 2002/0114920 | A1 * | 8/2002 | Scholz et al. | 428/119 |
| 2002/0128615 | A1 * | 9/2002 | Tyrrell et al. | 604/364 |
| 2002/0128621 | A1 * | 9/2002 | Kruchoski et al. | 604/385.01 |
| 2002/0177830 | A1 * | 11/2002 | Fernandez-Kleinlein et al. | 604/385.01 |
| 2003/0078554 | A1 * | 4/2003 | Drevik | 604/385.03 |
| 2003/0088222 | A1 * | 5/2003 | Yoshimasa et al. | 604/380 |
| 2004/0116018 | A1 * | 6/2004 | Fenwick et al. | 442/164 |
| 2004/0127877 | A1 * | 7/2004 | Odorzynski et al. | 604/385.03 |
| 2005/0143708 | A1 * | 6/2005 | Hagberg et al. | 604/385.18 |
| 2006/0046592 | A1 * | 3/2006 | Novelli | 442/59 |

FOREIGN PATENT DOCUMENTS

| | | |
|---|---|---|
| EP | 1 468 661 A1 | 10/2004 |
| GB | 2056283 A * | 3/1981 |
| WO | WO 99/15123 A1 | 4/1999 |
| WO | WO 99/65434 A1 | 12/1999 |
| WO | WO 00/00123 A1 | 1/2000 |
| WO | WO 00/01265 A1 | 1/2000 |
| WO | WO 00/40197 A1 | 7/2000 |
| WO | WO 01/36195 A1 | 5/2001 |
| WO | WO 02/20684 A2 | 3/2002 |

OTHER PUBLICATIONS

International Search Report PCT/US2005/037275 dated Mar. 17, 2006, 5 pages.

* cited by examiner ular example of a suitable topsheet 26 material can include a bonded-carded-web composed of polypropylene and polyethylene, such as has been used as a cover stock for KOTEX brand pantiliners, and has been obtainable

MULTILAYER ABSORBENT ARTICLE

FIELD OF THE INVENTION

The present invention relates to articles for use in contact with a tissue layer (e.g., skin) of the user. More particularly, the present invention pertains to an article having an engagement surface adapted to hold its position relative to a point on the tissue layer while inhibiting cutaneous damage.

BACKGROUND OF THE INVENTION

There are many articles that are intended to contact the skin of the user during use of the article. For example, absorbent articles, which contain discharged body exudates, contact the user's skin generally adjacent the source of the discharged exudate. In the case of some types of feminine care articles (i.e., sanitary napkins, pantiliners), it is well known to place the article adjacent a woman's pudendum during use to absorb and hold exudate, such as menses. Typical feminine care articles include various layers, such as a liquid pervious topsheet, a substantially liquid impervious backsheet joined to the topsheet, and an absorbent core 30 positioned and held between the topsheet and the backsheet.

Conventional topsheets of feminine care articles, which provide a body-facing surface for engagement with the user's skin, do not provide the desired binding energy. As a result, the topsheets do not assist in holding the article in place, or may cause damage and/or irritation to the user's skin. If the binding energy of the article with respect to the user's skin is too strong, movement of the article (e.g., removal) will cause skin cells of the outer layer of the skin to be removed, damaged, and/or irritated. If the binding energy of the article with respect to the user's skin is too weak, the article will easily move from its desired location thereby potentially allowing discharged body matter to circumvent the article. As a result, there has been a continued need for improved binding energies of feminine care articles and other articles that contact the skin of the user to minimize the cutaneous damage associate with the article while maintaining the article in its desired location.

BRIEF DESCRIPTION OF THE INVENTION

In one embodiment, an article for use in contact with a tissue layer of a person and capable of holding its position with respect to the contacted tissue layer while reducing the opportunity for damage to the tissue layer comprises a support structure and a contact layer associated with the support structure. The contact layer has an engagement surface adapted to contact the user's tissue layer and constructed so that the engagement surface has a first state adapted to inhibit movement of the article with respect to the tissue layer of the user, and a second state adapted to enhance movement of the article with respect to the tissue layer of the user. The engagement surface is adapted to transform from the first state to the second state upon application of a force greater than a threshold force.

In another embodiment, a contact layer for contacting the tissue layer of a user comprises an engagement surface adapted to contact the user's tissue layer. The contact layer is constructed so that the engagement surface has a first state adapted to inhibit movement of the contact layer with respect to the tissue layer of the user, and a second state adapted to enhance movement of the contact layer with respect to the tissue layer of the user. The engagement surface transforms from the first state to the second state upon application of a force greater than a threshold force.

Other features of the invention will be in part apparent and in part pointed out hereinafter.

BRIEF DESCRIPTION OF THE DRAWINGS

The various features, aspects and advantages of the present invention will become better understood with reference to the following description, appended claims and accompanying drawings where:

Corresponding reference characters indicate corresponding parts throughout the several views of the drawings.

DETAILED DESCRIPTION OF THE INVENTION

Figure 1:
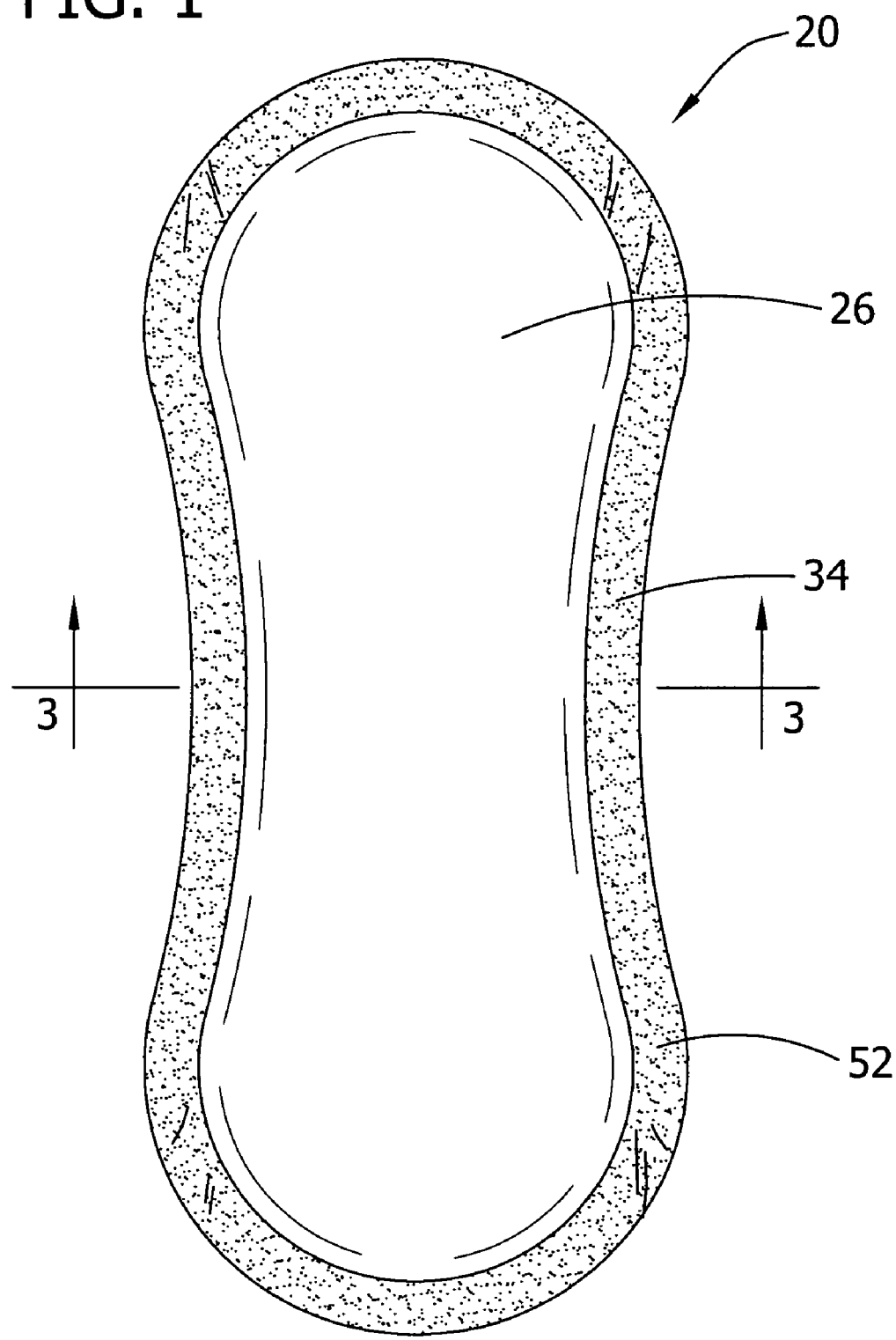
FIG. 1 is a top plan of a feminine napkin of the present invention.
Figure 2:
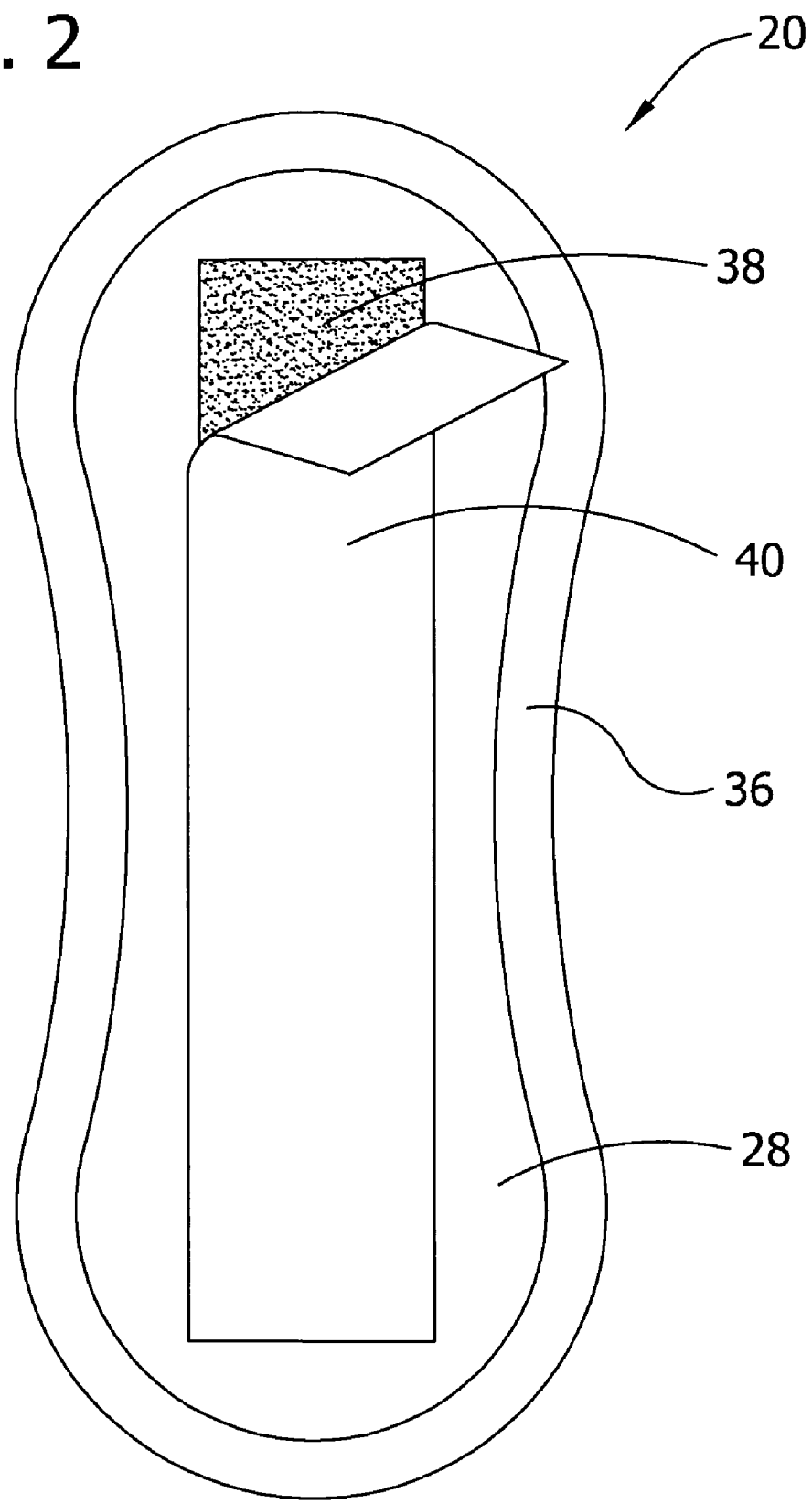
FIG. 2 is a bottom plan of the napkin.
Figure 3:
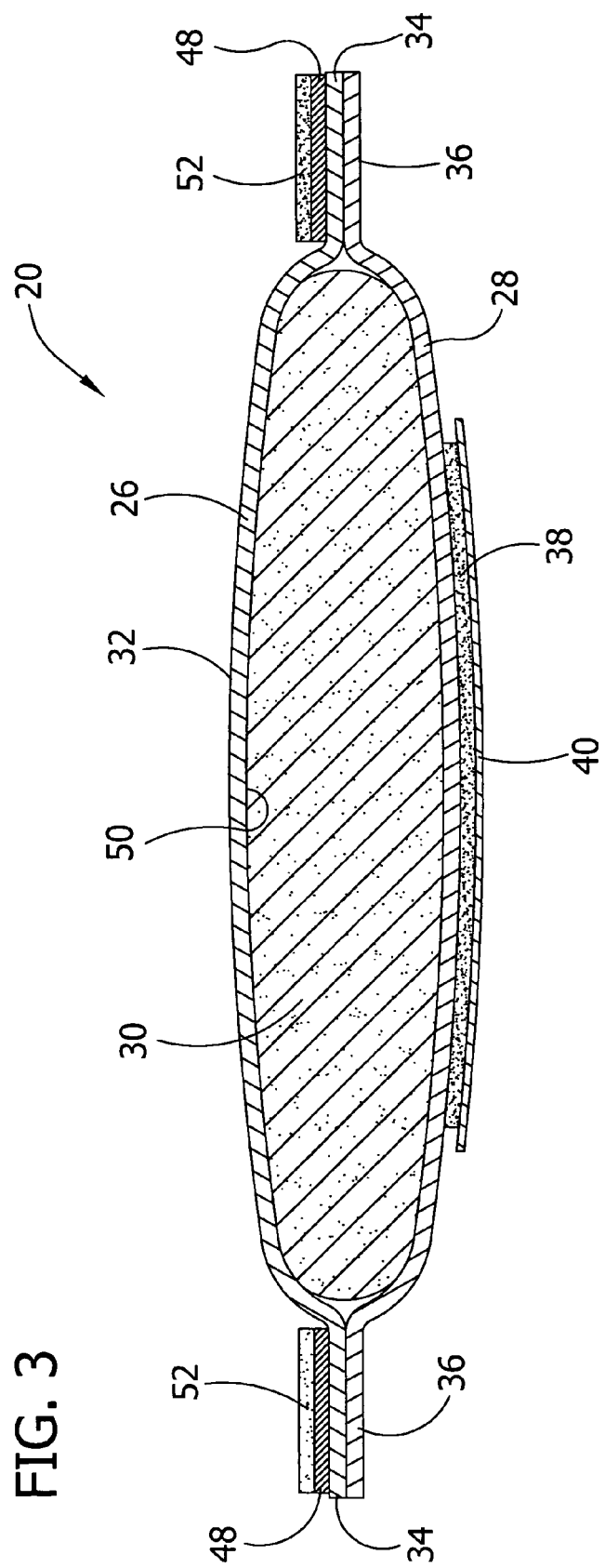
FIG. 3 is a section taken in the plane of line 3-3 of FIG. 1.

FIG. 1 illustrates an example of an article, such as the representatively shown feminine care article, configured to incorporate the present invention. The feminine care article can, for example, be a feminine care pad or sanitary napkin, which is indicated generally at 20. As illustrated in FIGS. 1-3, the napkin 20 can include a topsheet 26, a backsheet 28, and an absorbent core 30 positioned between the topsheet and the backsheet. The topsheet 26 may include a layer constructed of any operative material, and may be a composite material. For example, the topsheet 26 can include a woven fabric, a nonwoven fabric, a polymer film, a film-fabric laminate or the like, as well as combinations thereof. As used herein, the term "nonwoven" refers to a fabric web that has a structure of individual fibers or filaments which are interlaid, but not in an identifiable repeating manner. Examples of a nonwoven fabric include spunbond fabric, meltblown fabric, coform fabric, a carded web, a bonded-carded-web, a bicomponent spunbond fabric or the like as well as combinations thereof.

For example, the topsheet 26 can include a woven fabric, a nonwoven fabric, a polymeric film that has been configured to be operatively liquid-permeable, or the like, as well as combinations thereof. Other examples of suitable materials for constructing the topsheet 26 can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable topsheet 26 material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

In a desired arrangement, the topsheet 26 can be configured to be operatively liquid-permeable with regard to the liquids that the napkin 20 is intended to absorb or otherwise handle. The operative liquid-permeability may, for example be provided by a plurality of pores, perforations, apertures or other openings, as well as combinations thereof, that are present or formed in the topsheet. The apertures or other openings can help increase the rate at which bodily liquids can move through the thickness of the topsheet 26 and penetrate into the other components of the napkin 20 (e.g., the absorbent core 30). The selected arrangement of liquid-permeability is desirably present at least on an operative portion of the topsheet 26 that is appointed for placement on the body-side of the napkin 20.

The topsheet 26 can provide comfort and conformability, and can function to direct bodily exudates away from the body and toward the absorbent core 30. In a desired feature, the topsheet 26 can be configured to retain little or no liquid in its structure, and can be configured to provide a relatively comfortable and non-irritating bodyside surface 32 (broadly, an "engagement surface") next to the tissue layer (i.e., skin) of a female wearer. The topsheet 26 can be constructed of any material easily penetrated by bodily fluids that contact the surface of the topsheet.

The topsheet 26 can also have at least a portion of its bodyside surface 32 treated with a surfactant to render the topsheet more hydrophilic. The surfactant can permit arriving bodily liquids to more readily penetrate the topsheet 26. The surfactant may also diminish the likelihood that the arriving bodily fluids, such as menstrual fluid, will flow off the topsheet 26 rather than penetrate through the topsheet into other components of the napkin 20 (e.g., the absorbent core 30). In a particular configuration, the surfactant can be substantially evenly distributed across at least a portion of the upper, bodyside surface 32 of the topsheet 26 that overlays the upper, bodyside surface of the absorbent core 30.

The topsheet 26 may be maintained in secured relation with the absorbent core 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the topsheet 26, or fusing at least portions of the adjacent surface of the topsheet to portions of the adjacent surface of the absorbent core 30.

The topsheet 26 typically extends over the upper, bodyside surface of the absorbent core 30, but can alternatively extend around the napkin 20 to partially or entirely, surround or enclose the absorbent core 30. Alternatively, the topsheet 26 and the backsheet 28 can have peripheral margins 34, 36 that extend outwardly beyond the terminal, peripheral edges of the absorbent core 30, and the extending margins can be joined together to partially or entirely, surround or enclose the absorbent core.

The backsheet 28 may include a layer constructed of any operative material, and may or may not have a selected level of liquid-permeability or liquid-impermeability, as desired. In a particular configuration, the backsheet 28 may be configured to provide an operatively liquid-impermeable backsheet structure. The backsheet 28 may, for example, include a polymeric film, a woven fabric, a nonwoven fabric or the like, as well as combinations or composites thereof. For example, the backsheet 28 may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Desirably, the backsheet 28 can operatively permit a sufficient passage of air and moisture vapor out of the napkin 20, particularly out of an absorbent core 30 while blocking the passage of bodily liquids. An example of a suitable backsheet 28 can include a breathable, microporous film, such as a HANJIN Breathable Baffle available from Hanjin Printing, Hanjin P&C Company Limited, a business having offices located in Sahvon-li.Jungan-mvu.Kongiu-City, Chung cheong nam-do, Republic of South Korea. The backsheet 28 material is a breathable film, which is white in color, dimple embossed and contains: 47.78% calcium carbonate, 2.22% $TiO_2$, and 50% polyethylene.

Bicomponent films or other multi-component films can also be used as backsheet 28 material, as well as woven and/or nonwoven fabrics which have been treated to render them operatively liquid-impermeable. Another suitable backsheet 28 material can include closed cell polyolefin foam. For example, closed cell polyethylene foam may be employed. Still another example of a backsheet 28 material would be a material that is similar to a polyethylene film which is used on commercially sold KOTEX brand pantiliners, and is obtainable from Pliant Corporation, a business having offices located in Schaumburg, Ill., USA.

The structure of the absorbent core 30 can be operatively configured to provide a desired level of absorbency or storage capacity. More particularly, the absorbent body can be configured to hold a liquid, such as urine, menses, complex liquid or the like, as well as combinations thereof. The absorbent core 30 can include a matrix of absorbent fibers and/or absorbent particulate material, and the absorbent fiber can include natural and/or synthetic fiber. Additionally, the absorbent core 30 may include one or more components that can modify menses or intermenstrual liquid.

The absorbent core 30 may also include superabsorbent material. Superabsorbent materials are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof.

The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may desirably be included in an appointed storage or retention portion of the absorbent system, and may optionally be employed in other components or portions of the napkin 20.

The absorbent core 30 can be arranged in any operative shape and/or design. For example, the absorbent core 30 may comprise a composite structure (not shown) having a selected plurality of strata or layers or a unitary structure. Moreover, the material of the absorbent core 30 can be selected and configured to provide desired liquid-intake properties to quickly absorb and pull liquid away from the body. Accordingly, the absorbent core 30 can provide the function of liquid intake and can also provide the functions of liquid distribution, spreading, liquid retention, and shape maintenance. The absorbent core 30 may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the absorbent core 30 may include one or more components that can modify menses or intermenstrual liquid.

In a particular arrangement, the absorbent core 30 can be a thermally-bonded, stabilized airlaid fibrous web available from Concert Fabrication (Concert code 225.1021), a business having offices located in Gatineaux, Quebec, Canada (e.g. Concert code 225.1021). The absorbent core 30 may also be a similar, stabilized airlaid fibrous web available from Buckeye Technologies, Inc., a business having offices located in Memphis, Tenn., U.S.A.

Additionally, a selected configuration of garment adhesive 38, such as the illustrated strip regions, may be distributed onto the garment-side surface of the napkin 20 to help secure the napkin to the undergarment (not shown). Typically, the garment adhesive 38 can be distributed over the garment-side surface of the backsheet 28, and one or more layers or sheets of release material 40 can be removably placed over the garment adhesive 38 during storage prior to use.

Figure 4:
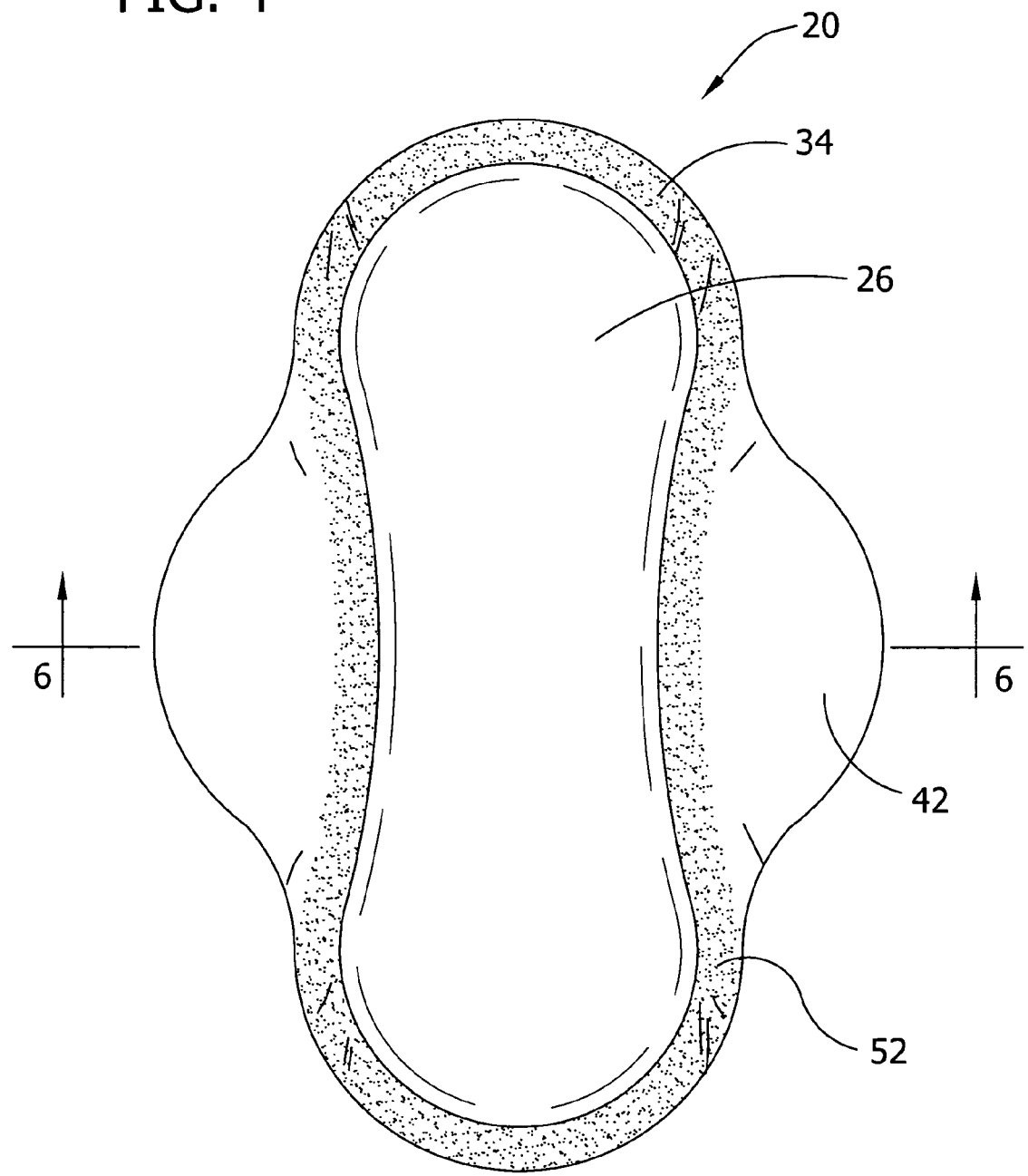
FIG. 4 is a top plan of another feminine napkin of the present invention having wings.
Figure 5:
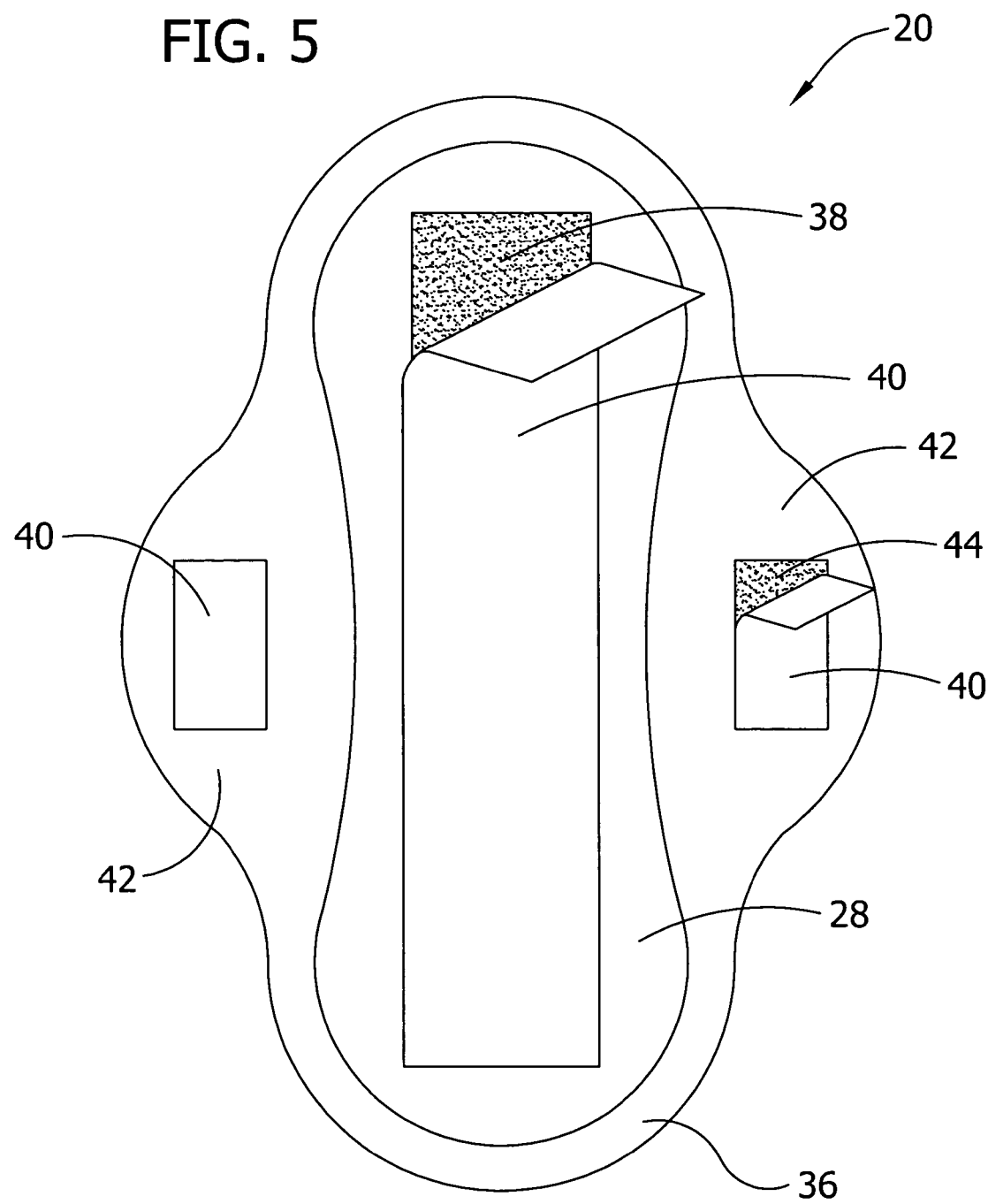
FIG. 5 is a bottom plan of the napkin shown in FIG. 4.
Figure 6:
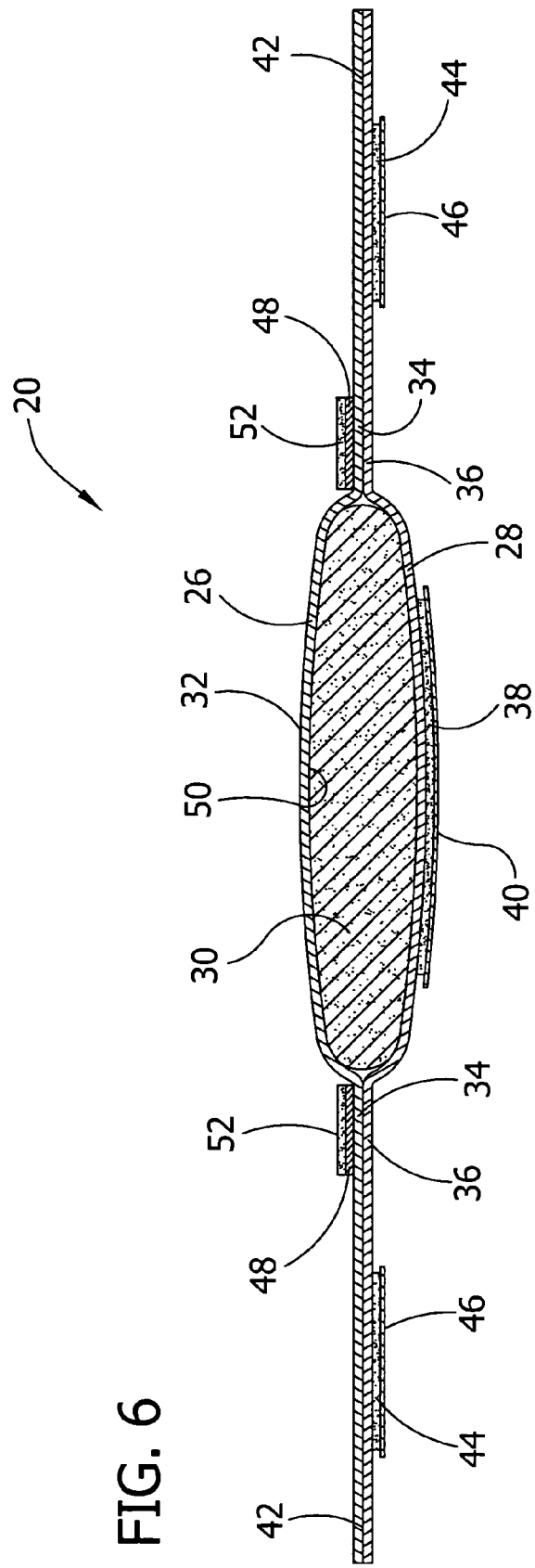
FIG. 6 is a section taken in the plane of line 6-6 of FIG. 4.

As illustrated in FIGS. 4-6, the napkin 20 can include a system of wing portions 42 which can be integrally connected to appointed sections of the napkin. After placing the napkin 20 in the undergarment, the wings 42 can be operatively wrapped and secured around the side edges of the undergarment to help hold the napkin in place as is know in the art. The wing portions 42 can be separately provided members that are subsequently attached or otherwise operatively joined to intermediate portions of the napkin 20.

In other configurations, the wing portions 42 can be unitarily formed with one or more components of the napkin 20. Either or both wing portions 42 may be formed from a corresponding, operative extension of the material employed to form the topsheet 26. Alternatively, either or both wing portions 42 may be formed from a corresponding, operative extension of the material employed to form the backsheet 28, or formed from a corresponding, operative combination of the topsheet 26 and backsheet materials.

The wing portions 42 can have any operative construction, and can include a layer of any operative material. Additionally, each wing portion 42 can comprise a composite material. For example, the wing portions 42 may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each wing portion 42 can be joined to its corresponding side region of the napkin 20 in any operative manner. For example, the wing portion can be joined to the topsheet 26, the backsheet 28 or another napkin 20 component, as well as any combination thereof. The wing portion 42 can be attached with hotmelt adhesive, but any other operative adhesive or attachment mechanism may alternatively be employed.

In another feature, each wing portion 42, or any desired combination of the employed wing portion, can include a panel-fastener component 44 which is operatively joined to an appointed engagement surface of its associated wing. The panel-fastener can be configured to operatively attach to the wearer's undergarment and/or to any appointed, landing-zone portion of the napkin 20. For example, the panel-fastener 44 can include a system of interengaging mechanical fasteners, a system of adhesive fasteners, a system of cohesive fasteners or the like, as well as combinations thereof.

With reference to FIGS. 5 and 6, for example, either or both wing portions 42 can include a panel-fastener system 44 that alternatively incorporates an operative garment adhesive. The garment adhesive may be a solvent-base adhesive, a hotmelt adhesive, a pressure-sensitive adhesive, or the like, as well as combinations thereof. Each section of garment adhesive may be covered with a removable release material 46.

In the construction of the napkin 20, the various components (e.g., topsheet 26, backsheet 28, absorbent core 30, wing portions 42) may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

In one configuration, the peripheral margin 34 of the bodyside surface 32 of the topsheet 26 has a lubricant 48 (broadly, "a sliding component") to allow the napkin 20 to slide along the user's skin without causing damage thereto. The lubricant 48 can be integrally formed within the napkin 20 or a substance applied to the napkin. In the illustrated configuration, the lubricant 48 is applied to the topsheet 26 and more specifically, the peripheral margin 34 (FIGS. 3 and 6). The lubricant 48 can be either continuously (e.g., line) or intermittently (e.g., dots, dashes) applied to the topsheet 26 or a portion thereof, such as, the peripheral margin 34. It is envisioned that the topsheet 26, or at least the peripheral margin 34, could be made of a low friction material. In that case, the topsheet material would be the "lubricant".

The lubricant 48 can be applied to either the bodyside surface 32 of the topsheet 26 or a backside 50 of the topsheet (i.e., the surface opposed to the bodyside surface) since the topsheet is liquid-permeable and the lubricant will permeate through the topsheet to the bodyside surface. In one configuration, the lubricant 48 is applied to the backside 50 of the topsheet 26 and allowed to permeate to the body-facing side. It is understood that other portions of the napkin 20 in addition to or besides the topsheet 26 can have the lubricant 48.

Examples of suitable lubricants 48 for applying to the napkin 20 include silicones, cyclomethicones, dimethicones, dimethiconol, PEG dimethicone, alkyl silicones, phenyl silicones, silicone phospholipids, silicone gums, silicone oils, silicone waxes, cyclopentasiloxane, dimethicone crosspolymers, and combinations thereof. Particular lubricants suitable for use on the topsheet include, for example, Dow Corning® 9041 Silicone Elastomer Blend Dimethicone(and) Crosspolymer, Dow Corning® 9011 Silicone Elastomer Blend, Dow Corning® 9040 Silicone Elastomer Blend-Cyclomethicone (and) Dimethicone Crosspolymer, Dow Corning® 9045 Silicone Elastomer Blend Cyclopentasiloxane (and) Dimethicone Crosspolymer, Dow Corning® 9509 Silicone Elastomer Suspension Dimethicone/Vinyl Dimethicone Crosspolymer (and) C12-14 Pareth-12, Dow Corning® 2503 Cosmetic Wax (Stearyl Dimethicone) Alkyl Methyl Siloxanes, Dow Corning® 556 Cosmetic Grade Fluid (polyphenylmethylsiloxane), Dow Corning® 929 Cationic Emulsion Amodimethicone (and) Tallowtrimonium Chloride (and) Nonoxynol-10, Dow Corning® HMW 2220 Non-ionic Emulsion Divinyldimethicone/Dimethicone Copolymer (and) C12-C13 Pareth-3 (and) C12-C13 Pareth-23, Dow Corning® 2-8177 Emulsion Amodimethicone (and) C12-C14 Sec-Pareth-7 (and) C12-C14 Sec-Pareth-5, all of which are available from Dow Corning of Midland, Mich., U.S.A. It is understood that other types of lubricants 48 could also be used to lower the dynamic coefficients of friction with respect to the skin of the user.

A body adhesive 52 (broadly, "a gripping component") is used to bind the napkin 20 to the skin of the user and maintain the napkin in its desired location during the use of the napkin (FIGS. 1, 2, 4 and 6). In one configuration, the body adhesive 52 is applied on the peripheral margin 34 of the topsheet 26 to cover the lubricant 48 applied thereto and prevent the static coefficient of friction from being substantially lowered by the lubricant. Ideally, the adhesional forces, which represent the force necessary to detach an object from the skin surface, of the body adhesive 52 are low enough to facilitate detachment of the napkin 20 from the skin before causing skin damage or pain. The body adhesive 52 may be covered with a releasable sheet (not shown) adapted to be removed by the user just prior to use to prevent the adhesive to adhering prematurely or to undesired surfaces.

Examples of suitable body adhesives 52 for applying to the topsheet 26 include polyvinylpyrrolidone (PVP) adhesive, vinylpyrrolidone/vinylimidazole copolymer, polyolefins, starch, casein/animal glue, natural rubber, styrenmic coploymers, polybutylene, acrylics, polyurethanes, polyesters, polyamides, bioadhesive polymers polyanionic polymers, and polyacrylic acid such as hydroxypropyl-cellulose and hydroxypropyl-methylcellulose. Additional suitable body adhesives 52 include cross-linked polyacrylic and polymethacrylic acids, which are described in European Patent Application EP 0 371 421 and blends of hydrophilic cellulose derivatives (40-95%) with polyethylene glycol (PEG), which are described in U.S. Pat. No. 4,713,243. Another suitable body adhesive 52 is a remoistenable and watersoluble hot-melt such as Luvitec® VPI55 K18P, which is available from BASF Corporation of Florham Park, N.J., U.S.A.

It is understood that other adhesives may be suitable for use as the body adhesive 52. Information on the adhesive and cohesive forces of different types of adhesives can be readily determined by one skilled in the art such as by using standard references (e.g., Handbook of Adhesives & Sealants published by McGraw-Hill Professional, 1999 or Handbook of Adhesive Chemicals and Compounding Ingredients published by Synapse Information Resources, 1998).

The combination of lubricant 48 and adhesive 52 on a napkin 20, results in the napkin having a surface 32 that engages the skin that has a first state, in which the napkin is adapted to inhibit movement with respect to the skin of the user, and a second state, which is adapted to enhance movement of the napkin with respect to the tissue layer of the user. Without being bound to any particular theory, it is believed that when the napkin 20 with both the lubricant 48 and the body adhesive 52 is applied to the user, the body adhesive binds the napkin to the skin of the user in the desired position. The static frictional force between the napkin 20 and the user's skin is directly related to the adhesional forces of the body adhesives 52, i.e., the strength of the bond between the body adhesive and the skin of the user. The body adhesive 52 also provides a lubricant impermeable layer or barrier to inhibit the lubricant 48 from contacting the skin of the user and lowering the static coefficient of friction. However, the engagement surface of the napkin 20 can be changed from the first state to the second state upon application of a force greater than a threshold force. Thus, when a force is applied to the napkin 20 that is greater than the adhesional forces of the body adhesive 52, the napkin will move with respect to the user's skin and the bond between the body adhesives and the user's skin will be broken. Upon breaking the bond between the body adhesive 52 and the user's skin, the barrier formed by the body adhesive will be ruptured thereby causing cracks, voids or other passageways in which the lubricant 48 can pass through the body adhesive layer and contact the skin of the user. In another configuration, breaking the bond between the body adhesive 52 and the user's skin displaces the body adhesive layer thereby exposing the lubricant 52 for contact with the user's skin. The lubricant 52 that comes into contact with the topsheet 26 of the napkin 20 and the skin of the user lowers the dynamic coefficient of friction and allows the napkin to move without damaging the skin of the user.

Generally speaking, frictional forces occur between any two contacting bodies where there are forces tending to slide one of the bodies relative to the other. The frictional forces act parallel to the contacting surfaces and opposite the forces tending to cause sliding between the bodies. Further, the frictional forces are proportional to normal forces on the bodies and to the tendency of the bodies to grip each other.

The coefficient of friction is the ratio of the frictional force between the bodies to the normal force between the bodies. The coefficient of friction is different between bodies at rest and bodies moving relative to each other. In general, two bodies contacting one another, but not moving relative to one another, will exhibit greater frictional resistance to motion than bodies that are moving relative to one another. Hence, a coefficient of static friction (i.e., coefficient of friction between bodies which are not moving relative to each other) is generally somewhat greater than a coefficient of dynamic friction (i.e., coefficient of friction between bodies which are moving relative to each other). However in conventional napkins, the difference is not believed to be large enough to have an effect on holding the napkin in place or protecting the skin from damage.

With respect to the present invention, the static coefficient of friction (i.e., in the first state) is about 5% to about 70% higher than the dynamic coefficient of friction (i.e., in the second state), preferably about 10% to about 55% higher, and more preferably, about 15% to about 35% higher.

Larger coefficients of friction correspond to larger amounts of friction between bodies, while smaller frictional coefficients correspond to smaller amounts of friction. In the case of products touching human skin, coefficients of friction that are too high cause higher shear forces at the skin surface, which can damage the skin and/or cause discomfort. In the illustrated embodiment, skin damage occurs when the adhesional forces between the napkin 20 and user's skin caused by the adhesive 52 are greater than the cohesive forces between the individual corneocytes (i.e., skin cells) of the stratum corneum (i.e., outer layer of the skin). As a result, the adhesional forces caused by the body adhesive 52 should be low enough to avoid separating corneocytes. In one configuration, the adhesional forces between the napkin 20 and the user's skin is about 5% to about 90% lower than the cohesive forces between the individual corneocytes, preferably about 15% to about 70% lower, and more preferably, about 25% to about 50% lower.

On the other hand, coefficients of friction that are too low allow the napkin 20 to easily move across the skin thereby possibly causing chafing of the skin or allowing the napkin to move from the desired position. Chafing is irritation of the stratum corneaum caused by friction generated by napkin 20 rubbing against the user's skin. Thus, the static coefficient of friction should be high enough to maintain the napkin 20 in place while the dynamic coefficient of friction should be low enough to minimize or inhibit damage to the skin, such as chafing, caused by the napkin moving across the user's skin.

To prevent damage to the skin of the user and/or dislodgement of the napkin 20, the adhesional forces between the user's skin and napkin should be greater than the force normally encountered during product wear (i.e., product displacement force). Movement of the napkin 20 during wear may cause discomfort, skin damage (e.g., chafing), lack of fit, and potentially leakage. In one configuration, the adhesional forces between the user's skin and the napkin is about 3% to about 60% higher than the product displacement force (i.e., the minimum amount of force required to overcome the skin-adhesive binding force that results in displacement of the napkin from the skin of the wearer) and more preferably, about 15% to about 30% higher.

The adhesional forces between the napkin 20 and the user's skin should also be lower than the force exerted during removal of the product (i.e., removal force) in order to allow easy product removal with minimal force and no pain. In one configuration, the removal force is about 5% to about 80% higher than the adhesional forces, preferably about 10% to about 65% higher, and more preferably about 20% to about 45% higher.

It is understood that the quantity of body adhesive 52 and lubricant 48 applied to the napkin 20 will vary depending of the types of body adhesive and lubricant selected and the desired static and dynamic coefficients of friction. However, the quantities of body adhesive 52 and lubricant 48 used should be sufficient to inhibit movement of the napkin 20 under normal activity of the user, and should allow the napkin to be removed from the user's skin without causing damage. In one configuration, the ratio of body adhesive 52 to lubricant 48 is in a range from about 25:1 to about 0.5:1. Preferably, the ratio of body adhesive 52 to lubricant 48 is in a range between about 10:1 and about 1:1, and more preferably the ratio is in a range between about 5:1 to about 2:1.

In another configuration, a moisturizer (not shown) is used in place of or in conjunction with the body adhesive 52 to increase the hydration level of the skin. Hydrating the user's skin will create a higher static coefficient of friction. The moisturizer can be used to cover a lubricant 48 as described in above with respect to the body adhesive 52. Certain lubricants 48, such as silicones, are known to have tendency to migrate to the surface with time. For articles that are worn or used for approximately the same period every time, the moisturizer and lubricant 48 can be selected so that migration of the lubricant through the moisturizer occurs approximately at the same time the product is scheduled to be removed. In another variation of this configuration, the moisturizer and lubricant 48 can be selected so that forces applied to the article allow the lubricant to migrate into contact with the user's skin and therefore ease the removal process.

Skin moisturizers may include, for example, humectants such as glycerin, propylene glycol, butylene glycol, low molecular weight polyethylene glycols, sorbitol, urea, sodium lactate, and the like. Skin moisturizers may also include occlusive agents such as petrolatum, mineral oil, paraffin wax, hydrogenated vegetable oils (e.g. palm, peanut, castor, canola), and the like. It is understood that the moisturizers can be applied to the napkin 20 using various application techniques such as spraying, slot coating, printing, and the like.

EXAMPLE

Figure 9:
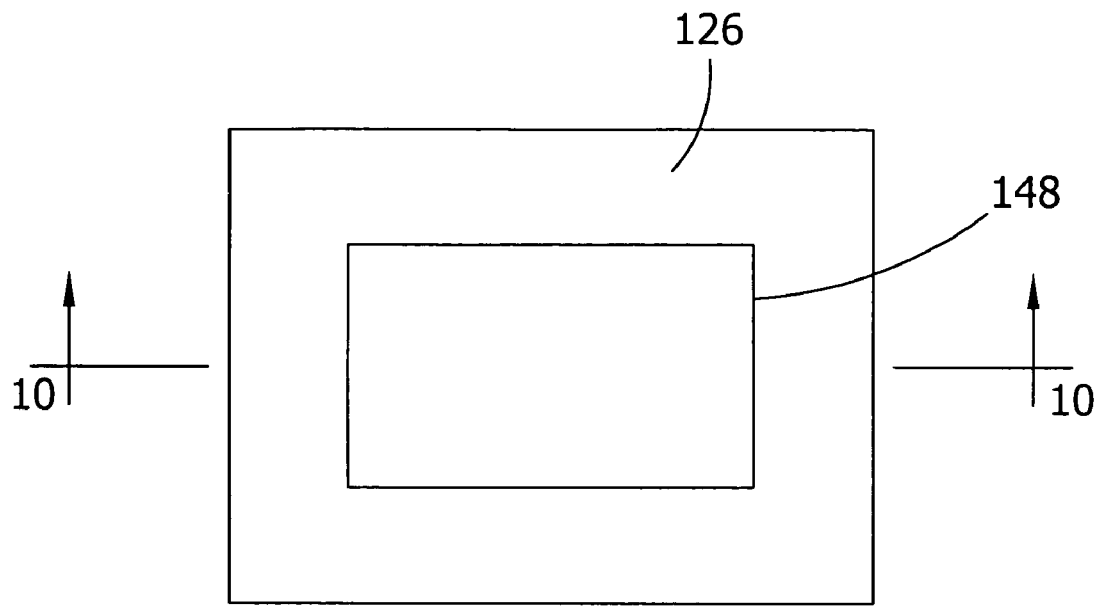
FIG. 9 is a top plan of a liner used in the testing apparatus.
Figure 10:
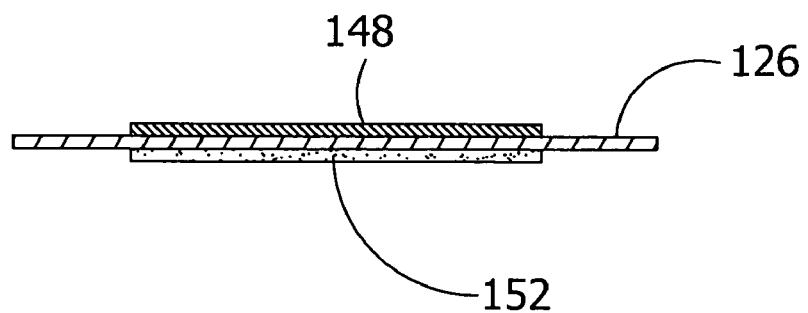
FIG. 10 is a section taken in the plane of line 10-10 of FIG. 9.

In this Example, a liner 126 having a lubricant 148 and an adhesive 152 applied thereto(referred to hereafter as "test liner") was tested to determine the static and dynamic frictional forces between the liner 126 and a human skin simulant 128 (FIGS. 9 and 10). The liner 126 was a non-woven liner manufactured by Kimberly-Clark Corporation of Neenah, Wis. under the product name Lexington Spunbond. The material selected for use as the liner 126 is suitable for contacting the skin of the user of an article. For example, the material used for liner 126 can be used as the body-contacting material in sanitary napkins, such as topsheet 26 of napkin 20, diapers, or other similar articles. The liner 126 was cut into twenty-one 6-centimeter by 8-centimeter sections.

Sixteen of the liner sections were evenly coated on a skin-facing surface of the liner 126 with about 0.5 grams of the adhesive 152. The adhesive was a glue available from the American Glue Corporation of Taylor, Mich. as Kidstik and described in U.S. Pat. No. 4,954,544.

A lubricant 148 was then applied to eight of the sixteen sections. About 0.25 grams of lubricant was used to evenly coat a backside of the test liners 126 (i.e., the side opposite the adhesive). The lubricant 148 was Dow Corning® 9040 Silicone Elastomer Blend available from Dow Corning of Midland, Mich., U.S.A.

Figure 7:
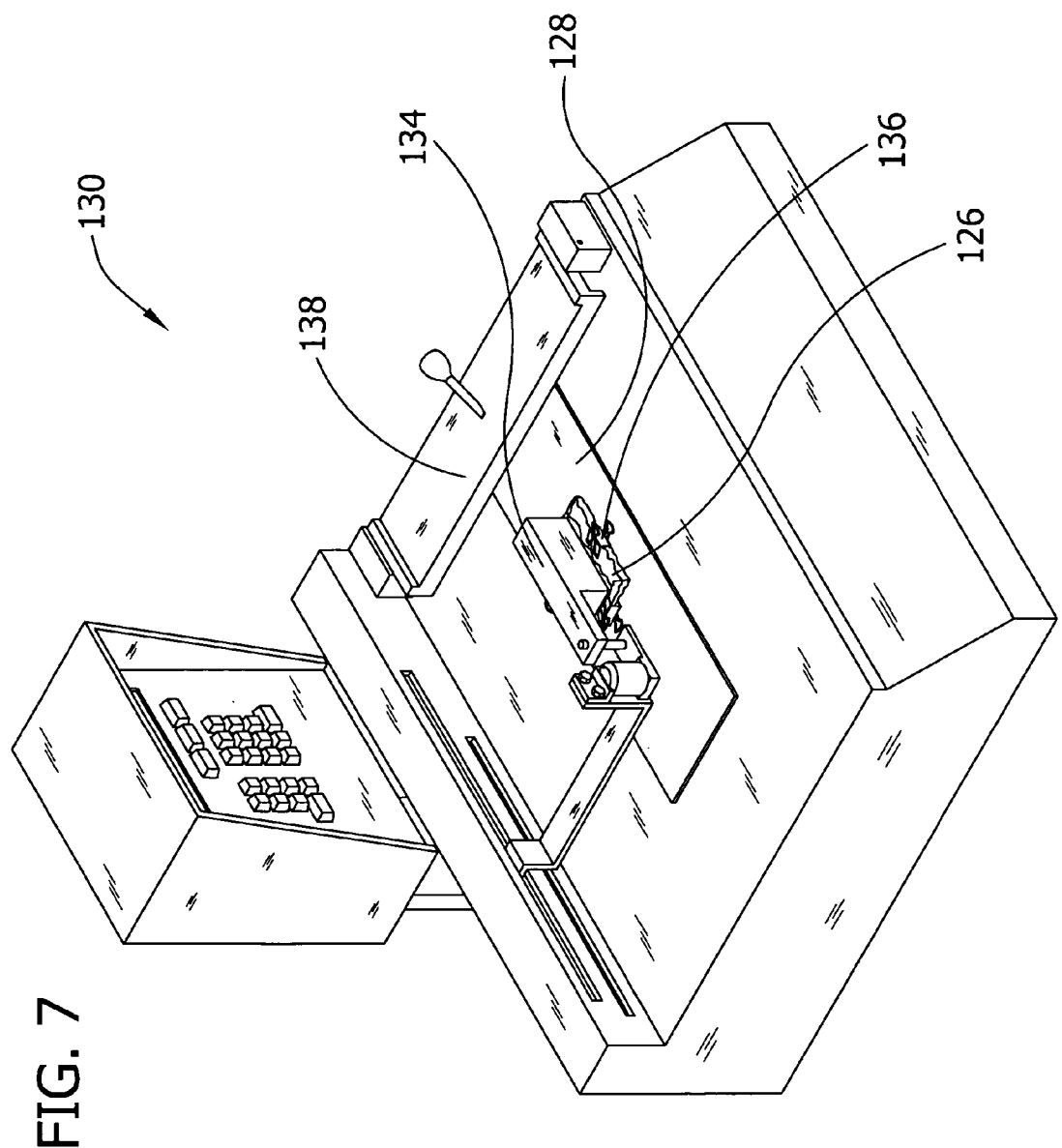
FIG. 7 is a perspective of a testing apparatus for testing the static and dynamic frictional forces of a contact layer of the present with respect to a skin simulant.
Figure 8:
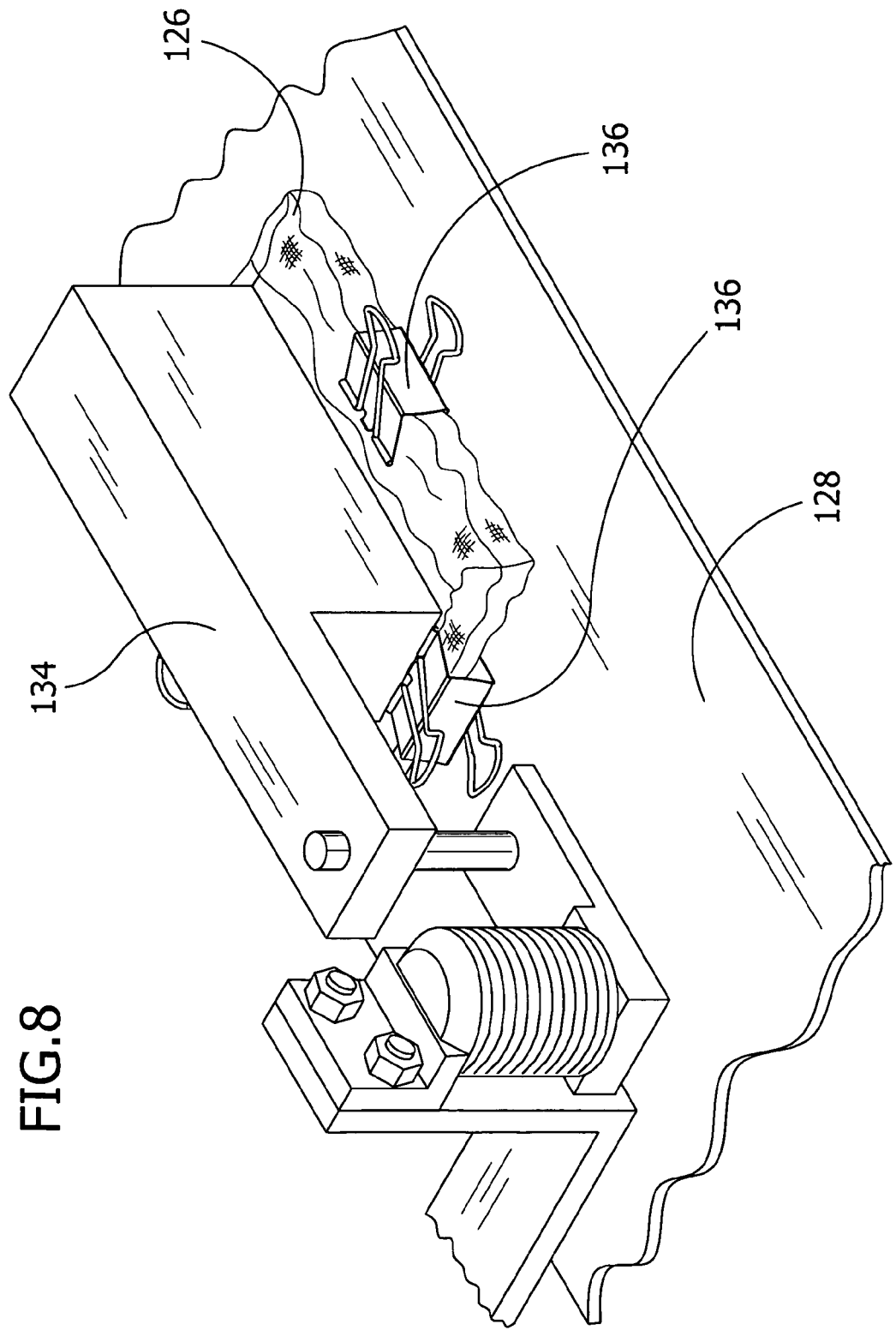
FIG. 8 is an enlarged fragmentary perspective of the testing apparatus of FIG. 7.

With reference to FIGS. 7 and 8, a Monitor/Slip and Friction™ instrument, available as Model 32-06-00 from Testing Machines Inc. of Ronkonkoma, N.Y., U.S.A. was used to conduct frictional force measurements and is indicated generally at 130. The slip and friction instrument 130 was calibrated before every use as specified by the manufacturer (FIG. 7). A modified sled 134 was custom made to have a bottom surface area of 5 centimeters by 3 centimeters and a weight of 73 grams. The test liners 126 were attached to the sled 134 using three clips 136 so that the adhesive 152 was facing outwardly away from the sled (FIG. 8). One clip 136 was secured to top and the other two to opposite sides. The grips of the clips were bent upward so that they did not interfere with the test results. The clips 136 were three mini binder clips available from EXP of Broomfield, Colo., U.S.A. The slip and friction instrument 130 was set to move the sled 134 at a rate of 38.1 centimeters/minute, and to stop after traveling 8.25 centimeters. A 1000-gram weight was placed on the sled 134 before testing began to add extra weight. The normal force was set at 1074 grams to account for the sled 134, the 1000-gram weight, test liner 126, and clips 136 used to secure the liner to the sled.

A 5-centimeter by 15-centimeter piece of skin simulant 128, which was obtained from SiliClone Studio, of Valley Forge, Pa., U.S.A., was secured to the instrument 130 with the slip and friction instrument sample retaining clip 138. The sled 134, with the test liner 126 attached, was placed into its position on the instrument 130 and lined up over the skin simulant 128. In order to assure consistency, all tests were performed in an environmentally controlled room having a temperature of 23° C. and 50% relative humidity. In addition, the skin simulant 128 was cleaned with alcohol and allowed to dry before each test.

All twenty-one test liners 126 (i.e., eight liners with adhesive, eight liners with adhesive and glue, and five untreated liners) were tested to determine the static and dynamic frictional forces between each of the liners and the skin simulant 128. The data obtained from the testing is summary in the following tables (Tables 1-3) and was used to generate the force curves of FIG. 11.

The static frictional force (i.e., the force applied to start the liner moving) is the measurement at the apex of the initial peak. With reference to Tables 1-3, the static frictional forces are the friction value in gram-force at time equal one second. The dynamic friction forces (i.e., the force applied to keep the liner moving at 38.1 centimeters/minute) was measured at several points and are provided in Tables 1-3 as the friction values in gram-force between 2 seconds and 10 seconds. The static and dynamic frictional forces for each set of test liners 126 (i.e., eight liners with adhesive, eight liners with adhesive and glue, and five untreated liners) were averaged (Tables 1-3). The force curves of FIG. 11 were generated using the averaged data.

TABLE 1

Data results from testing of the Liner.

| | Frictional Force (gf) | | | | | |
|---|---|---|---|---|---|---|
| Time (s) | Liner a | Liner b | Liner c | Liner d | Liner e | Avg |
| 0 | 0 | 0 | 0 | 0 | 0 | 0 |
| 1 | 758.1 | 880.1 | 864.1 | 893.7 | 881.2 | 713.0 |
| 2 | 743.8 | 879.4 | 865.8 | 885.4 | 874.2 | 708.4 |
| 3 | 741.8 | 867.6 | 861.0 | 877 | 867.2 | 702.9 |
| 4 | 734.8 | 854.3 | 856.8 | 856.1 | 853.3 | 693.2 |
| 5 | 738.3 | 849.8 | 849.5 | 847.0 | 845.3 | 689.1 |
| 6 | 741.1 | 836.2 | 841.1 | 836.2 | 840.0 | 683.4 |
| 7 | 736.9 | 828.2 | 838.7 | 831.0 | 834.8 | 679.4 |
| 8 | 736.2 | 826.8 | 824.4 | 831.7 | 821.2 | 674.7 |
| 9 | 722.9 | 815.6 | 816.7 | 828.9 | 814.9 | 668.0 |
| 10 | 726.1 | 812.9 | 812.2 | 820.9 | 808.0 | 665.0 |

TABLE 2

Data results from testing of the Liner with adhesive applied thereto.

| | Frictional Force (gf) | | | | | | | | |
|---|---|---|---|---|---|---|---|---|---|
| Time (s) | Liner a | Liner b | Liner c | Liner d | Liner e | Liner f | Liner g | Liner h | Avg |
| 0 | 0 | 0 | 0 | 0 | 0 | 0 | 0 | 0 | 0 |
| 1 | 737.6 | 630.6 | 680.8 | 624.6 | 642.8 | 712.1 | 721.5 | 691.2 | 604.7 |
| 2 | 642.4 | 600.9 | 637.9 | 625.3 | 574.8 | 639.6 | 657.4 | 656.7 | 559.7 |
| 3 | 644.5 | 594.0 | 615.2 | 607.9 | 564.7 | 648.7 | 660.2 | 638.6 | 553.0 |
| 4 | 645.9 | 590.1 | 589.4 | 598.8 | 571.0 | 653.6 | 665.1 | 611.4 | 547.7 |
| 5 | 621.9 | 580.7 | 571.0 | 614.5 | 595.4 | 657.1 | 675.2 | 589.1 | 545.5 |
| 6 | 610.0 | 559.5 | 550.7 | 607.6 | 598.8 | 665.3 | 680.4 | 580.4 | 539.3 |
| 7 | 605.8 | 553.5 | 533.3 | 581.1 | 594.7 | 670.6 | 681.5 | 580.4 | 534.2 |
| 8 | 610.7 | 545.9 | 513.1 | 553.2 | 573.8 | 660.9 | 687.0 | 577.2 | 525.5 |
| 9 | 607.2 | 531.2 | 510.7 | 539.9 | 557.4 | 636.5 | 680.8 | 462.2 | 503.9 |
| 10 | 582.8 | 480.0 | 494.6 | 532.6 | 552.8 | 597.1 | 643.6 | 560.9 | 495.5 |

TABLE 3

Data results from testing of the Liner with adhesive and glue applied thereto.

| | Frictional Force (gf) | | | | | | | | |
|---|---|---|---|---|---|---|---|---|---|
| Time (s) | Liner a | Liner b | Liner c | Liner d | Liner e | Liner f | Liner g | Liner h | Avg |
| 0 | 0 | 0 | 0 | 0 | 0 | 0 | 0 | 0 | 0 |
| 1 | 521.1 | 484.2 | 459.1 | 482.8 | 423.5 | 447.2 | 451.8 | 558.1 | 425.4 |
| 2 | 369.9 | 229.4 | 284.8 | 275.4 | 301.2 | 327.7 | 228.0 | 304.0 | 258.0 |
| 3 | 276.4 | 130.0 | 228.0 | 183.7 | 175.7 | 284.5 | 176.8 | 275.0 | 192.6 |
| 4 | 255.9 | 109.5 | 206.4 | 156.5 | 147.8 | 281.7 | 173.6 | 269.8 | 178.4 |
| 5 | 248.9 | 101.5 | 192.4 | 160.0 | 155.5 | 281.1 | 190.3 | 259.7 | 177.1 |
| 6 | 258.3 | 100.8 | 192.4 | 167.7 | 153.4 | 271.9 | 197.7 | 261.5 | 178.9 |
| 7 | 276.1 | 105.3 | 216.1 | 169.4 | 171.2 | 266.7 | 199.1 | 268.1 | 186.6 |
| 8 | 282.7 | 102.9 | 224.2 | 178.1 | 184.4 | 260.1 | 205.3 | 282.4 | 192.0 |
| 9 | 294.9 | 105.7 | 218.2 | 186.9 | 181.3 | 253.4 | 203.6 | 292.5 | 193.9 |
| 10 | 289.0 | 99.7 | 228.0 | 197.3 | 184.4 | 262.5 | 211.3 | 310.2 | 199.2 |

Figure 11:
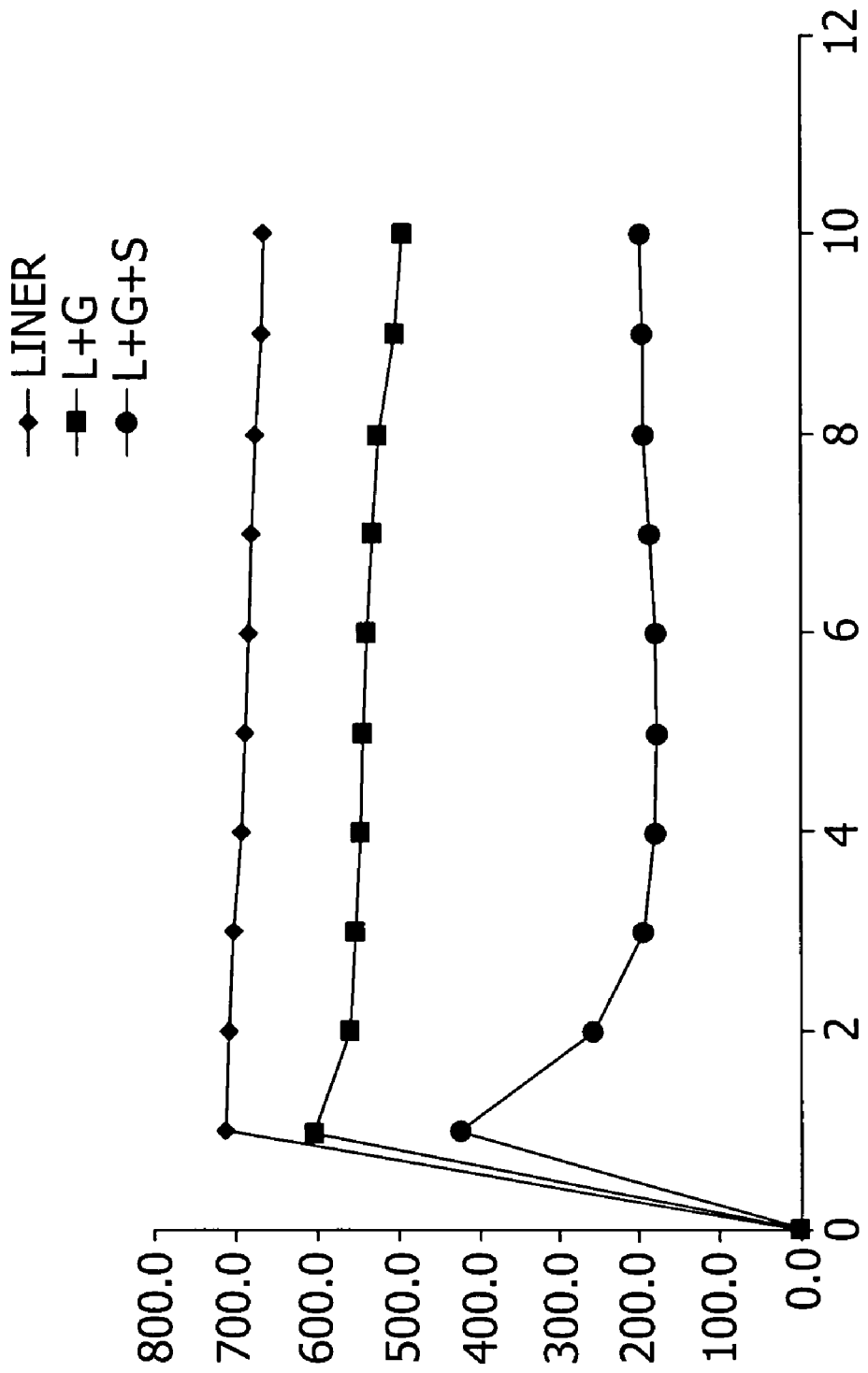
FIG. 11 is a graph depicting the static and dynamic frictional forces between the contact layer and the skin simulant.

FIG. 11 is a graphic illustration of the static and dynamic frictional forces between the sets of test liners 126 and the skin simulant 128. Each curve represents one of the sets. The liner only test is shown using diamond data points and is labeled as "LINER". As shown, both the static and dynamic frictional forces between the liner and the skin simulant 128 are relatively high. Thus, these liners had a relatively high threshold force (i.e., the force necessary to initiate movement of the liner with respect to the skin simulant 128) and once moving required a relatively high force to keep the liner in motion. Accordingly, if the skin simulant 128 was actual skin, damage to the skin may have been caused by abrasion from the liner rubbing across the skin.

The liner and adhesive test set is shown with square data points and labeled "L+G". While the liners with adhesive had slightly lower static and dynamic frictional forces, they were still relatively high. Accordingly, the liners with adhesive also required a high force to initiate and maintain movement of the material on the skin simulant 128. Thus, real skin may have been damaged upon and during movement of the liner by abrasion.

The liner with lubricant and adhesive is shown with circular data points and is labeled "L+G+S". As shown, the static frictional force, while less than the previous two sets, is still elevated while the dynamic frictional force is substantially lower. As a result, the liner with lubricant and adhesive required a relatively large amount of energy required to initiate movement (i.e., a relatively high threshold force). However, the required force would not be so high as to cause skin damage. The amount of energy required to maintain the liner in motion was relatively low which would allow the liner to travel across the skin of the user without damaging the skin due to abrasion.

It is contemplated that the features of the invention presented herein may applied to, but not limited to, other feminine care products (e.g., interlabial pads, tampons, pantiliners), diapers, training garments, incontinence articles, bandages, wound care dressings, breast pads, face masks, eye patches, transdermal/topical drug delivery patches/devices, medical diagnostic equipment attachments (e.g. electrocardiograph), ostomy care products, surgical tapes, and intravenous, endotracheal or other catheters/tubes. In all cases the product is capable of holding itself in place relative to the adjacent tissue, but if motion is initiated the product acts to reduce frictional interaction with the tissue.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. An article for personal wear in contact with a tissue layer of a wearer and capable of holding its position with respect to the contacted tissue layer while reducing the opportunity for damage to the tissue layer, the article having an outer surface and comprising a body-facing engagement surface opposite the outer surface for contacting the wearer's tissue layer, the engagement surface having a first state adapted to inhibit movement of the article with respect to the tissue layer of the wearer, and a second state adapted to enhance movement of the article with respect to said tissue layer, said engagement surface being adapted to transform from the first state to the second state upon application of a force greater than a threshold force, the engagement surface comprising a gripping component and a sliding component wherein the gripping component overlies the sliding component in the first state;
wherein the static coefficient of friction of the engagement surface in the first state is substantially greater than the dynamic coefficient of friction of the engagement surface in the second state;
the gripping component is disposed for engaging and gripping the tissue layer in the first state until a force greater than the threshold force is encountered which transforms the engagement surface whereby the sliding component is brought into engagement with the tissue layer to promote relative sliding motion between the engagement surface and the tissue layer; and
the gripping component includes a body adhesive.

2. The article as set forth in claim 1 wherein the gripping component is disposed to shield the tissue layer from contact with the sliding component in the first state and is displaced to expose the sliding component for contact with the tissue layer in the second state.

3. The article as set forth in claim 2 wherein the gripping component is deformed upon application of a force greater than the threshold force for exposing the sliding component to the tissue layer.

4. The article as set forth in claim 3 wherein the gripping component is ruptured upon application of a force greater than the threshold force.

5. The article as set forth in claim 1 wherein the static and dynamic coefficients of friction of the engagement surface are selected to inhibit damage to the user's tissue layer caused by the engagement surface being in contact with the tissue layer.

6. The article as set forth in claim 2 wherein the static coefficient of friction of the engagement surface in the first state is about 5% to about 90% greater than the dynamic coefficient of friction of the engagement surface in the second state.

7. The article as set forth in claim 6 wherein the static coefficient of friction of the engagement surface in the first state is about 15% to about 70% greater than the dynamic coefficient of friction of the engagement surface in the second state.

8. The article as set forth in claim 7 wherein the static coefficient of friction of the engagement surface in the first state is about 25% to about 50% greater than the dynamic coefficient of friction of the engagement surface in the second state.

9. The article as set forth in claim 1 wherein the sliding component comprises a lubricant.

10. The article as set forth in claim 9 wherein the lubricant is selected from a group consisting of silicone, cyclomethicones, dimethicones, dimethiconol, PEG dimethicone, alkyl silicones, phenyl silicones, silicone phospholipids, silicone gums, silicone oils, silicone waxes, cyclopentasiloxane, dimethicone crosspolymers, and combinations thereof.

11. The article as set forth in claim 1 wherein the article is selected from a group consisting of interlabial pads, incontinence devices, menstrual pads, diapers, training garments, bandages, drug delivery patches, medical diagnostic equipment attachments, ostomy care products, surgical tape, wound care dressings, breast pads, face masks, and eye patches.

12. The article as set forth in claim 1 wherein the threshold force is selected to minimize cutaneous damage.

13. An article for personal wear comprising an engagement surface for contacting a tissue layer of a wearer, the engagement surface comprising a lubricant and a body adhesive overlying the lubricant, the engagement surface having a first state adapted to inhibit movement of the article with respect to the tissue layer of the wearer wherein the body adhesive adheres the article directly to the tissue layer of the wearer, the engagement surface being adapted to transform from the first state to a second state upon application of a force greater than a threshold force, the second state being adapted to enhance movement of the article with respect to the tissue layer wherein the lubricant is brought into engagement with the tissue layer to promote relative sliding motion between the article and the tissue layer;
wherein the article has an outer surface;
the engagement surface is a body-facing surface;
the engagement surface is opposite the outer surface; and
the static coefficient of friction of the engagement surface in the first state is substantially greater than the dynamic coefficient of friction of the engagement surface in the second state.

14. The article as set forth in claim 13 wherein the body adhesive is disposed to shield the tissue layer from contact with the sliding component in the first state and is displaced to expose the lubricant for contact with the tissue layer in the second state.

15. The article as set forth in claim 14 wherein the body adhesive is deformed upon application of a force greater than the threshold force for exposing the lubricant.

16. The article as set forth in claim 15 wherein the body adhesive is ruptured upon application of a force greater than the threshold force.

\* \* \* \* \*